United States Patent [19]

Ando

[11] Patent Number: 4,707,343

[45] Date of Patent: Nov. 17, 1987

[54] APPARATUS FOR STERILIZING CONTACT LENSES

[75] Inventor: Tetsuya Ando, Kyoto, Japan

[73] Assignee: Senju Pharmaceutical Co., Ltd., Osaka, Japan

[21] Appl. No.: 821,616

[22] Filed: Jan. 23, 1986

[30] Foreign Application Priority Data

Nov. 27, 1984 [JP] Japan .................. 59-250786

[51] Int. Cl.⁴ ............................................... A61L 2/04
[52] U.S. Cl. ..................................... 422/300; 422/307; 206/5.1; 219/328
[58] Field of Search ........................ 422/300, 302, 307; 206/5.1; 219/328, 379, 386; 337/320, 393, 397

[56] References Cited

U.S. PATENT DOCUMENTS

| 3,080,756 | 3/1963 | Baker ........................... 337/393 X |
| 3,771,088 | 11/1973 | Sliger .......................... 337/393 X |
| 3,783,429 | 1/1974 | Otte .............................. 337/393 |
| 3,801,278 | 4/1974 | Wagner et al. ............... 422/300 X |
| 3,961,893 | 6/1976 | Russell et al. ................ 422/300 |
| 3,973,760 | 8/1976 | Browning et al. ........... 219/328 X |
| 3,983,362 | 9/1976 | Hoogesteger et al. ...... 422/300 X |
| 4,013,410 | 3/1977 | Thomas et al. .............. 422/300 X |
| 4,158,126 | 6/1979 | Seitz ............................. 219/328 X |
| 4,178,499 | 12/1979 | Bowen ......................... 219/328 X |
| 4,242,304 | 12/1980 | Ryder ........................... 422/300 X |
| 4,243,632 | 1/1981 | Ryder ........................... 422/300 X |
| 4,251,719 | 2/1981 | Ryder ........................... 422/300 X |
| 4,256,952 | 3/1981 | Thomas et al. .............. 422/300 X |
| 4,302,664 | 11/1981 | Ryder et al. ................. 422/307 X |
| 4,303,828 | 12/1981 | Thomas et al. .............. 422/307 X |
| 4,307,289 | 12/1981 | Thomas et al. .............. 422/300 X |
| 4,379,965 | 4/1983 | Dounce et al. ............... 422/300 X |
| 4,381,285 | 4/1983 | Wittenberg ................... 422/300 X |
| 4,388,521 | 6/1983 | Thomas et al. .............. 422/302 X |
| 4,492,854 | 1/1985 | Ryder et al. ................. 422/307 X |
| 4,529,868 | 7/1985 | Bowen et al. ................ 422/307 X |
| 4,576,798 | 3/1986 | Hall et al. .................... 422/300 X |
| 4,578,566 | 3/1986 | Bowen ......................... 422/307 X |
| 4,582,076 | 4/1986 | Prat .............................. 422/300 X |

FOREIGN PATENT DOCUMENTS

| 21828 | 1/1981 | European Pat. Off. ............ 422/300 |
| 2369847 | 7/1978 | France ................................. 422/300 |
| 207507 | 10/1924 | United Kingdom . |
| 872784 | 7/1961 | United Kingdom . |
| 880110 | 10/1961 | United Kingdom . |
| 1128955 | 10/1968 | United Kingdom . |
| 2097593 | 11/1982 | United Kingdom . |
| 2108430 | 5/1983 | United Kingdom . |

Primary Examiner—Barry S. Richman
Assistant Examiner—Jill Johnston
Attorney, Agent, or Firm—James N. Videbeck

[57] ABSTRACT

An apparatus for heat-sterilizing contact lenses, particularly soft lenses includes a housing having a sterilizing chamber, a heater for heating the sterilizing chamber, and a temperature sensor adapted to detect the temperature of the sterilizing chamber. The temperature sensor comprises a flexible sensor container, a material sealed into the sensor container, and a sealing end portion. The material sealed in the container has a melting point or liquefaction point corresponding to the temperature in a zone surrounding the sterilizing chamber. The sealing end portion has a mechanism for interrupting heating when the detected temperature reaches a predetermined level.

3 Claims, 12 Drawing Figures

APPARATUS FOR STERILIZING CONTACT LENSES

The present invention relates to an apparatus for sterilizing contact lenses, particularly soft contact lenses. Soft contact lenses have to be disinfected at least once a day, for otherwise bacteria may settle and grow on them to cause untoward effects on the eyes.

For the disinfection of contact lenses, it is common practice to heat-sterilize them in a disinfectant fluid, e.g. physiological saline, in a sterilizing vessel at 90° to 98° C. for 15 to 25 minutes.

The sterilizing apparatus heretofore employed for this purpose comprises a sterilizing vessel containing a disinfectant fluid and a heating plate associated with an electric heater, and soft contact lenses to be sterilized are put in the sterilizing vessel which is then placed on the heating plate to thereby heatsterilize the lenses. The heating plate is connected to a thermostat which is adapted to sense the temperature of the heating plate and, when the temperature has reached a preset level, open the heater circuit to allow the lenses to be further heat-sterilized for a certain time by the residual heat of the heating plate and sterilizing vessel.

However, as the sterilizing vessel is generally built compactly, the thermal capacitance of the whole sterilizing apparatus is not so large. Moreover, since the low ambient atmospheric temperature causes a rapid drop of temperature of the apparatus, the sterilizing vessel and the heating plate also suffer rapid decreases in temperature so that the temperature necessary for heat sterilization cannot be retained for a necessary time period. Accordingly, the sterilization of soft contact lenses tends to be insufficient. In addition, because the sterilizing apparatus is miniaturized, the instrumentation and switching mechanism of the heating system are complicated of necessity so that electrical troubles, particularly faults associated with the thermostat occur frequently.

The present invention, which was developed to overcome these disadvantages of the prior art apparatus, has as one of its objects the provision of a sterilizing apparatus which has a remarkably improved sterilizing performance.

It is another object of the present invention to provide a contact lens sterilizing apparatus which is conducive to a minimum of temperature change by way of maintaining a zone surrounding a sterilizing chamber at a predetermined temperature so as to prevent direct dissipation of the residual heat in the apparatus.

It is still another object of the present invention to provide a sterilizing apparatus which is free from electrical troubles by way of employing a novel circuit breaker system which comprises a temperature sensor adapted to detect the temperature accurately for an exact switching function in association with a highly reliable microswitch.

The contact lens sterilizing apparatus according to the present invention comprises a housing having a sterilizing chamber, heating means for heating said sterilizing chamber, and a temperature sensor adapted to detect the internal temperature of said sterilizing chamber, said temperature sensor comprising a flexible sensor container, a material sealed into said sensor container and having a melting or liquefaction point corresponding to the temperature in a zone surrounding said sterilizing chamber, and a sealing end portion for sealing said sensor container, said sealing end portion having means for interrupting heating when the detected temperature reaches a predetermined level.

Preferably, said heating means for heating said sterilizing chamber comprises heating plate means disposed externally of wall means defining said heating chamber and heater means secured to said heating plate means and comprising positive characteristic thermisters.

Preferably, said flexible sensor container is bellows-shaped.

Preferably, said material having a melting or liquefaction point corresponding to the temperature in said zone surrounding said sterilizing chamber is microcrystalline wax.

Preferably, said means for interrupting heating at a predetermined level consists of an engageable projection provided at said sealing end portion of said sensor container and an associated actuating lever of a microswitch which is engageable therewith.

An embodiment of the present invention will hereinafter be described with reference to the accompanying drawings. It should, however, be understood that the invention is by no means limited to the particular embodiment.

FIG. 7 shows the sterilizing vessel, in which (a) is a plan view and (b) is a cross-sectional view.

FIG. 9 (a), (b) and (c) are side-elevation views of the main components for explaining the function of the circuit breaker system.

The contact lens sterilizing apparatus 1 according to the present invention comprises a housing 2 made of synthetic resin or other suitable material and an internal system which is described hereinafter.

Figure 1:
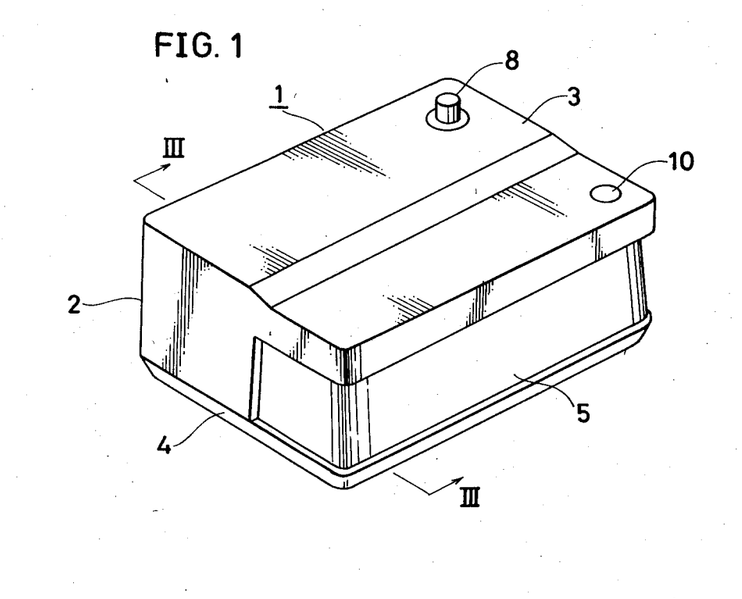
FIG. 1 is a perspective exterior view of the contact lens sterilizing apparatus according to an embodiment of the present invention.
Figure 2:
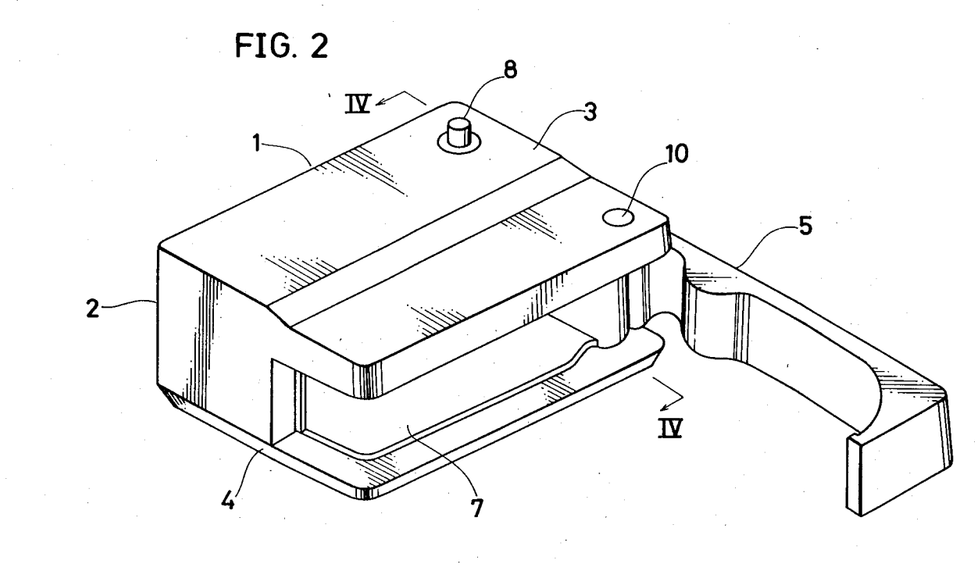
FIG. 2 is a perspective exterior view showing the same apparatus with its door opened.
Figure 7A:
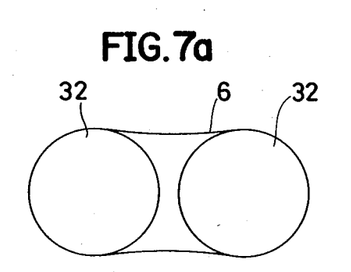
Figure 7B:
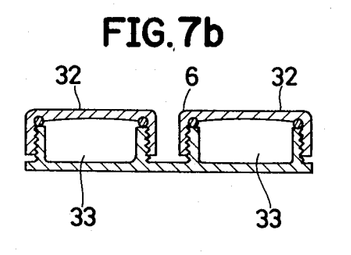

As shown in FIGS. 1 and 2, the housing 2 consists of a body 3, a bottom cover 4 and a door 5 which can be opened and closed about a pivot at one side. Behind the door 5, there is a sterilizing chamber 7 in which a sterilizing vessel 6, which is shown in FIG. 7 (a), (b), is positioned for heat sterilization. The sterilizing vessel 6 is made of heat-resistant synthetic resin such as polycarbonate resin. Projecting from the body 3 is a push button 8, depression of which actuates a microswitch 9 disposed in the housing 2. A pilot lamp 10 adapted to indicate the passage of an electric current is provided at the front end of the body 3.

Figure 3:
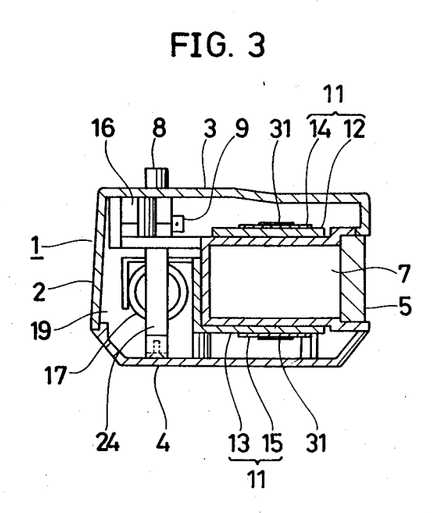
FIG. 3 is a cross-sectional view taken along the line III—III of FIG. 1.
Figure 4:
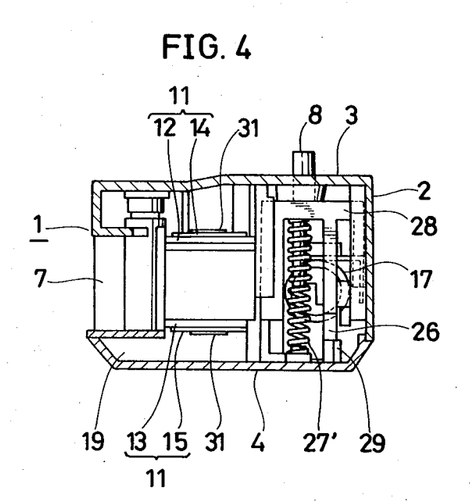
FIG. 4 is a cross-sectional view taken along the line IV—IV of FIG. 2.

Referring to FIGS. 3 and 4, heating means 11 are provided externally of top, bottom and rear partitioning wall means defining the sterilizing chamber 7. The heating means 11 comprises a top heating plate 12, a bottom heating plate 13, and a top heater 14 and a lower heater 15 which are secured to said heating plates, respectively. The top and bottom heating plates 12, 13 are each made of metal such as iron, brass or the like and the top and bottom heaters 14, 15 are positive-characteristic thermisters. The power is led in via a socket 16.

Figure 5:
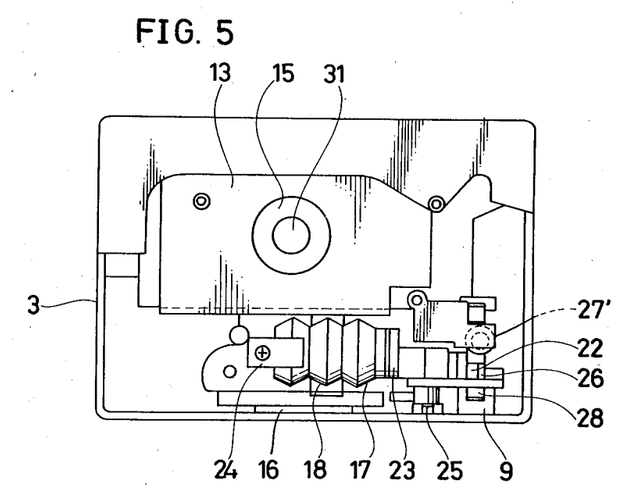
FIG. 5 is a view showing the reverse side with the bottom cover detached.
Figure 6:
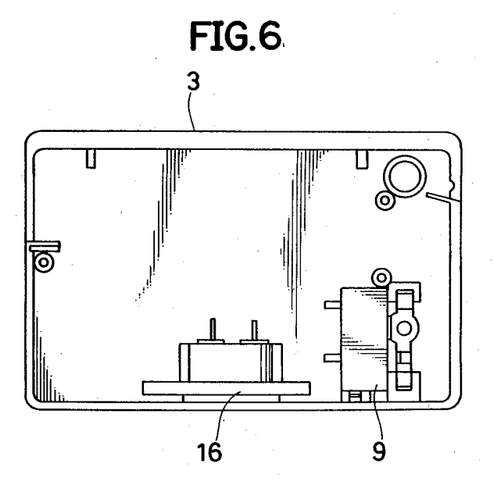
FIG. 6 is a view showing the inside of the outer housing.
Figure 8:
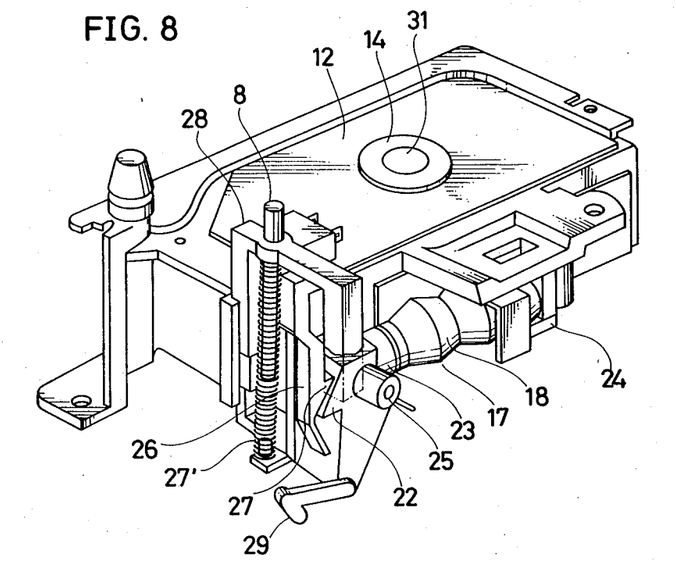
FIG. 8 is a partially exploded perspective view showing the main part of the sterilizing apparatus.

Referring to FIGS. 5 and 8, a temperature sensor 17 is disposed adjacent to the sterilizing chamber 7. This temperature sensor 17 is supported by a retention member 24 in such a manner that its rear portion is vertically swingable, while its front end is pivotally supported by a pin 25. As better shown in FIG. 9, the temperature sensor 17 comprises a sensor container 18, a body of wax 20 sealed into the container, and a seal member 23 which seals off the front end of the sensor container. The sensor container 18 is made in a bellows-like configuration from a flexible synthetic resin such as silicone resin. The wax 20 is preferably a microcrystalline wax having a melting point corresponding to the temperature within a zone 19 surrounding the sterilizing chamber 7. The seal member 23 is equipped with a rod member 21 whose displacement is dependent upon the degree of softening or hardening of the wax 20, and an outer engageable projection 22.

The engageable projection 22 of the temperature sensor 17 is engaged by an actuating lever 26. The actuating lever 26 is connected to the forward end of the push button 8 and has an engageable pawl 27 which engages said engageable projection 22. The actuating lever 26 is normally biased upwardly by a spring 27'. The actuating lever 26 is guided by a guide frame 28 at its upper end and supported by a support lever 29 at its lower end. The microswitch 9, push-button 8, actuating lever 26, temperature sensor 17 and spring 27', taken together, constitute a circuit breaker system 30.

Though not shown, one terminal of the socket 16 is electrically connected to the electrode plate 31 of said top and bottom heaters 14, 15, while the other terminal is connected to one terminal of said microswitch 9. The other terminal of said microswitch 9 is connected to the top and bottom heating plates 12, 13. Thus, there is completed a heating circuit of socket 16—microswitch 9—top and bottom heaters 14, 15—top and bottom heating plates 12, 13—socket 16. Similarly, there is completed a display circuit of top heater 14—pilot lamp 10—top heating plate 12.

The function of the contact lens sterilizing apparatus will be explained below.

Referring, first, to FIG. 7, both covers 32 of the sterilizing vessel 6 are removed and a disinfectant fluid is poured into recesses 33. The soft contact lenses are immersed in the disinfectant fluid and the covers 32 are replaced. The sterilizing vessel 6 is then set in the sterilizing chamber 7 and the door 5 is closed. Then, the push-button 8 is pressed until it is locked in the lower position.

Figure 9A:
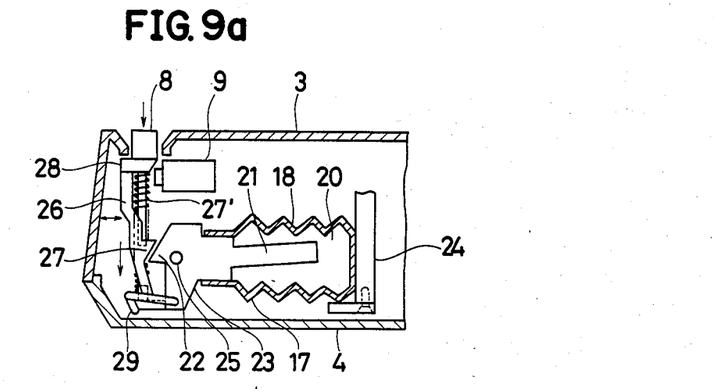
Figure 9B:
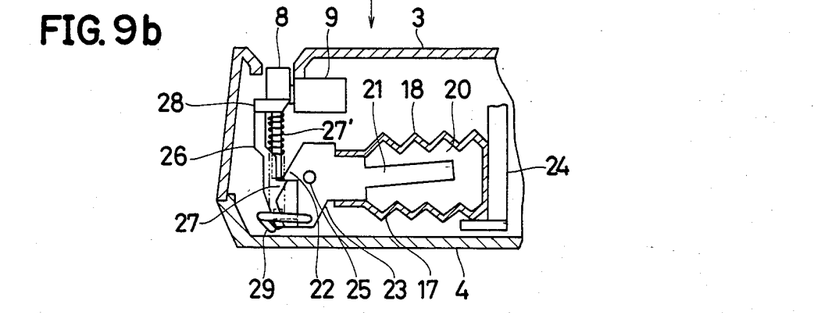

When the push-button 8 is pressed [FIG. 9 (a)] against the biasing force of the spring 27', it descends to actuate the microswitch 9, whereby the heating circuit is closed to start heating and, at the same time, the pilot lamp 10 is energized. As the push-button 8 is pressed, the actuating lever 26 also descends so that its pawl 27 rides over the engageable projection 22 of the temperature sensor 17 and is then engaged by the projection 22 underneath thereof, so as to lock the push-button 8 and actuating lever 26 [FIG. 9 (b)].

Figure 9C:
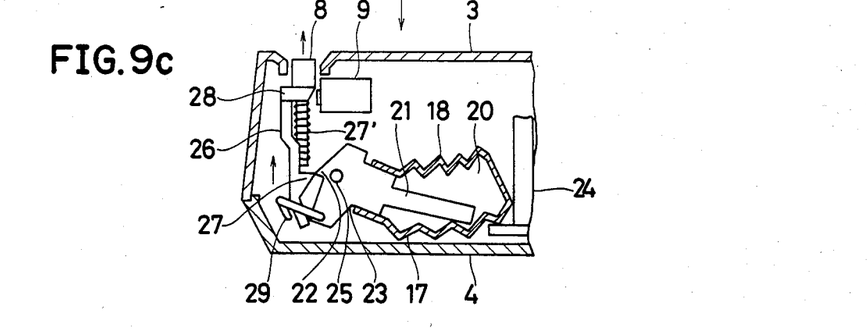

As a current flows through the heating circuit and the temperature of top and bottom heating plates 12, 13 and top and bottom heaters 14, 15 rises, the radiant heat causes the zone 19 to be heated, with the result that the temperature sensor 17 is also heated. As the temperature of zone 19 and sensor container 18 reaches and exceeds the melting point of the wax 20, the wax 20 starts melting and becomes soft as a whole. In this state, the upward force applied against the engageable projection 22 by spring 27' via the pawl 27 deforms the sensor container 18 about the pin 25 in such a manner that the engageable pawl 27 is released from the engageable projection 22. As the actuating lever 26 and push-button 8 ascend together under the action of spring 27' [FIG. 9 (c)], the microswitch 9 is actuated to open the heating circuit, whereupon heating is discontinued and the pilot lamp 10 goes off.

After lapse of a predetermined period of time after automatic reset of the push-button 8, the sterilizing vessel 6 is taken out. The above sequence of events complete a heat sterilization of soft contact lenses.

According to the present invention, once the proper material to be sealed into the temperature sensor 17 is selected and its melting point or liquefaction temperature is known, the sterilizing apparatus detects the retention temperature accurately. Moreover, as the liquefaction time can be set by selecting the proper internal volume (the mass of the substance sealed in) and manner of installation of the sensor container 18, the device can be used as a useful timer and switching mechanism.

Further, since positive-characteristic thermisters are used as heaters 14, 15 in the sterilizing apparatus of the present embodiment, there is no risk of the sterilizing chamber 7 being overheated. Moreover, as the temperature sensor 17 ensures a positive opening of the heating circuit, the temperature of the sterilizing vessel 6 can be maintained substantially at a predetermined level for a predetermined time period.

Furthermore, as the zone 19 surrounding the sterilizing chamber 7 accommodating the heating means 11 and circuit breaker system 30 is maintained at a predetermined temperature so as to prevent direct dissipation of the residual heat of the sterilizing vessel 6 into the atmosphere, the temperature change of the sterilizing vessel 6 can be held to a minimum.

Moreover, the apparatus is so designed that the circuit for the heating means 11 is opened by the microswitch 9 which is driven by the temperature sensor 17, with the result that chances of electrical troubles are substantially nil· as compared with the conventional apparatus.

While, in the temperature sensor 17 of the exemplary embodiment described above, a microcrystalline wax 20 having a melting point corresponding to the retention temperature of the zone 19 was utilized, any other material having a melting or liquefaction point similar to that of wax 20 may of course be employed with equal success.

I claim:
1. A contact lens sterilizing apparatus comprising:
a housing,
wall means defining a sterilizing chamber disposed on said housing,
heating means for heating said sterilizing chamber, said heating means comprising heating plate means disposed externally of said wall means and including a positive character thermistor secured thereto,
a temperature sensor adapted to detect the temperature of said sterilizing chamber, said temperature sensor comprising a flexible sensor container, a material sealed into said sensor container and having a melting or liquification point corresponding to a predetermined temperature, and a seal member for sealing said sensor container, said seal member including a pivotal mounting for rotationally mounting said seal member on said housing, and including a rod projecting into said sealed material and whose rotational displacement around said pivotal mounting is dependent upon the softening or hardening of said sealed material, and a projection projecting outwardly from the seal member, an actuating lever comprising a push button which projects from said housing, a spring which biases said actuating lever upwardly, and a pawl which is engageble with said projection of said seal member to releasably retain said actuating lever in an activated position when the temperature of said sterilizing chamber is below said predetermined temperature, and a microswitch which is engageable with said push button, and said pawl to activate and deactivate said heating means.

2. A contact lens sterilizing apparatus according to claim 1 wherein said flexible sensor container is bellows-shaped.

3. A contact lens sterilizing apparatus according to claim 1 wherein said material having a melting or liquefaction point corresponding to the predetermined temperature is microcrystalline wax.

* * * * *